(12) United States Patent
Raab et al.

(10) Patent No.: US 10,953,196 B2
(45) Date of Patent: Mar. 23, 2021

(54) CATHETER HUBS

(71) Applicant: BOSTON SCIENTIFIC SCIMED, INC., Maple Grove, MN (US)

(72) Inventors: David Raab, Minneapolis, MN (US); Ajay Gupta, Shoreview, MN (US); Mark S. Smith, Coon Rapids, MN (US); James M. Anderson, Corcoran, MN (US); Ken Fredrikson, Howard Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 514 days.

(21) Appl. No.: 15/704,751

(22) Filed: Sep. 14, 2017

(65) Prior Publication Data
US 2018/0071484 A1 Mar. 15, 2018

Related U.S. Application Data

(60) Provisional application No. 62/394,473, filed on Sep. 14, 2016.

(51) Int. Cl.
*A61M 25/00* (2006.01)
(52) U.S. Cl.
CPC . *A61M 25/0097* (2013.01); *A61M 2025/0098* (2013.01); *A61M 2207/00* (2013.01)
(58) Field of Classification Search
CPC ................................................. A61M 25/0097
USPC ........................................................ 604/533
See application file for complete search history.

(56) References Cited

U.S. PATENT DOCUMENTS

| 4,968,300 | A | 11/1990 | Moutafis et al. |
| 5,224,939 | A | 7/1993 | Holman et al. |
| 5,380,301 | A | 1/1995 | Prichard et al. |
| 5,830,401 | A | 11/1998 | Prichard et al. |
| 6,245,044 | B1 * | 6/2001 | Daw ................... A61B 17/3401 604/158 |
| 7,367,980 | B2 | 5/2008 | Kida et al. |
| 7,713,260 | B2 | 5/2010 | Lessard et al. |

(Continued)

FOREIGN PATENT DOCUMENTS

| WO | 9401161 A1 | 1/1994 |
| WO | 0040282 A1 | 7/2000 |

(Continued)

OTHER PUBLICATIONS

International Search Report and Written Opinion dated Dec. 8, 2017 for International Application No. PCT/US2017/051595.

*Primary Examiner* — Brandy S Lee
*Assistant Examiner* — Nidah M Hussain
(74) *Attorney, Agent, or Firm* — Seager, Tufte & Wickhem, LLP

(57) ABSTRACT

A hub assembly for connection to a medical device. The hub assembly may comprises an outer component having a proximal end, a distal end, and a cavity extending from the proximal end to the distal end. The hub assembly may further include an insert having a proximal end, a distal end, and a lumen extending from the proximal end to the distal end positioned at least in part within the cavity of the outer component. The insert may have a lumen extending from the proximal end to the distal end thereof. The outer component may be formed from a first material and the insert may be formed from a second material different from the first material.

13 Claims, 12 Drawing Sheets

(56) References Cited

U.S. PATENT DOCUMENTS

| | | | |
|---|---|---|---|
| 7,896,853 B2 | 3/2011 | Triplett et al. | |
| 8,105,315 B2 | 1/2012 | Johnson et al. | |
| 8,123,759 B2 | 2/2012 | Kida et al. | |
| 8,357,127 B2 | 1/2013 | Triplett et al. | |
| 8,469,953 B2 | 6/2013 | DeCarlo | |
| 8,986,283 B2 | 3/2015 | Rajendran et al. | |
| 2001/0049503 A1 | 12/2001 | Estabrook et al. | |
| 2003/0220628 A1* | 11/2003 | Klisch | A61M 25/0097 604/524 |
| 2004/0181273 A1 | 9/2004 | Brasington et al. | |
| 2005/0059958 A1 | 3/2005 | Lessard et al. | |
| 2005/0070878 A1 | 3/2005 | Triplett et al. | |
| 2005/0245963 A1* | 11/2005 | Kida | A61B 17/12113 606/200 |
| 2006/0052750 A1 | 3/2006 | Lenker et al. | |
| 2006/0217655 A1* | 9/2006 | Vitullo | A61N 1/36017 604/21 |
| 2007/0021648 A1 | 1/2007 | Lenker et al. | |
| 2008/0108976 A1 | 5/2008 | Johnson et al. | |
| 2008/0183183 A1 | 7/2008 | Kida et al. | |
| 2009/0177114 A1 | 7/2009 | Chin et al. | |
| 2010/0121345 A1 | 5/2010 | Brasington et al. | |
| 2011/0143014 A1* | 6/2011 | Stankus | A61F 2/958 427/2.14 |
| 2011/0306843 A1 | 12/2011 | Lenker et al. | |
| 2012/0197200 A1* | 8/2012 | Belson | A61M 25/0097 604/164.12 |
| 2013/0205584 A1 | 8/2013 | Pham et al. | |
| 2013/0261399 A1 | 10/2013 | Lenker et al. | |
| 2014/0025039 A1 | 1/2014 | Rajendran et al. | |
| 2014/0073926 A1 | 3/2014 | Rajendran et al. | |
| 2014/0081210 A1 | 3/2014 | Bierman et al. | |
| 2014/0207069 A1 | 7/2014 | Bierman et al. | |
| 2014/0257042 A1 | 9/2014 | Lenker et al. | |
| 2014/0276432 A1 | 9/2014 | Bierman et al. | |
| 2015/0151089 A1* | 6/2015 | Tan | A61M 39/0693 604/508 |
| 2015/0351793 A1 | 12/2015 | Bierman et al. | |
| 2017/0197059 A1* | 7/2017 | Toyota | A61M 25/0054 |

FOREIGN PATENT DOCUMENTS

| | | |
|---|---|---|
| WO | 2004080286 A2 | 9/2004 |
| WO | 2005025661 A2 | 3/2005 |
| WO | 2005035040 A1 | 4/2005 |
| WO | 2006031582 A2 | 3/2006 |
| WO | 2007120109 A1 | 10/2007 |
| WO | 2008057666 A2 | 5/2008 |
| WO | 2009067661 A1 | 5/2009 |
| WO | 2012159000 A2 | 11/2012 |
| WO | 2013119565 A1 | 8/2013 |
| WO | 2014074237 A1 | 5/2014 |
| WO | 2015133281 A1 | 9/2015 |
| WO | 2015136423 A1 | 9/2015 |

* cited by examiner

CATHETER HUBS

CROSS REFERENCE TO RELATED APPLICATIONS

This application claims the benefit of provisional U.S. Patent Application No. 62/394,473, filed on Sep. 14, 2016, which is hereby incorporated by reference in its entirety.

TECHNOLOGY FIELD

The present application relates generally to a hub, and in particular, to a microcatheter hub.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing methods, and use alternatives for medical devices.

In a first example, a hub assembly for connection to a medical device may comprise an outer component having a proximal end, a distal end, and a cavity extending from the proximal end to the distal end and an insert having a proximal end, a distal end, and a lumen extending from the proximal end to the distal end positioned at least in part within the cavity of the outer component. The insert may have a lumen extending from the proximal end to the distal end thereof. The outer component may be formed from a first material and the insert may be formed from a second material different from the first material.

Alternatively or additionally to any of the examples above, in another example, the second material may be more compliant than the first material.

Alternatively or additionally to any of the examples above, in another example, the hub assembly may further comprise one or more windows extending through a wall of the outer component.

Alternatively or additionally to any of the examples above, in another example, the one or more windows may be filled with a compliant material to form one or more elastically deformable regions in the outer component.

Alternatively or additionally to any of the examples above, in another example, the one or more elastically deformable regions may form a unitary structure with the insert.

Alternatively or additionally to any of the examples above, in another example, the one or more elastically deformable regions may be separate components from the insert.

Alternatively or additionally to any of the examples above, in another example, the hub assembly may further comprise a clamping mechanism configured to be removably positioned over the one or more elastically deformable regions.

Alternatively or additionally to any of the examples above, in another example, the clamping mechanism may be configured to exert biasing force on an outer surface of the one or more elastically deformable regions to deform the one or more elastically deformable regions towards a center of the outer component.

Alternatively or additionally to any of the examples above, in another example, the clamping mechanism may comprise a "c" clip.

Alternatively or additionally to any of the examples above, in another example, the distal end of the insert may extend distally beyond the distal end of the outer component.

Alternatively or additionally to any of the examples above, in another example, a portion of the insert may extend distally beyond the distal end of the outer component forms a tapered strain relief portion.

Alternatively or additionally to any of the examples above, in another example, the distal end of the outer component may be configured to be coupled to a medical device.

Alternatively or additionally to any of the examples above, in another example, when coupled, a distal opening of the medical device may be configured to be adjacent to the proximal end of the insert.

Alternatively or additionally to any of the examples above, in another example, at least a portion of a surface of the lumen of the insert may comprise a texturizing characteristic.

Alternatively or additionally to any of the examples above, in another example, the texturizing characteristic may be configured to increase friction between the insert and a medical device configured to be inserted into the lumen of the insert.

In another example, a hub assembly for connection to a medical device may comprise an outer component having a proximal end, a distal end, and a cavity extending from the proximal end to the distal end and an insert having a proximal end, a distal end, and a lumen extending from the proximal end to the distal end positioned at least in part within the cavity of the outer component, the insert having a lumen extending from the proximal end to the distal end thereof. The outer component may be formed from a first material and the insert may be formed from a second material different from the first material.

Alternatively or additionally to any of the examples above, in another example, the second material may be more compliant than the first material.

Alternatively or additionally to any of the examples above, in another example, the hub assembly may further comprise one or more windows extending through a wall of the outer component.

Alternatively or additionally to any of the examples above, in another example the one or more windows may be filled with a compliant material to form one or more elastically deformable regions in the outer component.

Alternatively or additionally to any of the examples above, in another example, the one or more elastically deformable regions may form a unitary structure with the insert.

Alternatively or additionally to any of the examples above, in another example, the one or more elastically deformable regions may be separate components from the insert.

Alternatively or additionally to any of the examples above, in another example, the hub assembly may further comprise a clamping mechanism configured to be removably positioned over the one or more elastically deformable regions.

Alternatively or additionally to any of the examples above, in another example, the clamping mechanism may be configured to exert biasing force on an outer surface of the one or more elastically deformable regions to deform the one or more elastically deformable regions towards a center of the outer component.

Alternatively or additionally to any of the examples above, in another example, the distal end of the insert may extend distally beyond the distal end of the outer component.

Alternatively or additionally to any of the examples above, in another example, a portion of the insert extending distally beyond the distal end of the outer component may form a tapered strain relief portion.

Alternatively or additionally to any of the examples above, in another example, the distal end of the outer component may be configured to be coupled to a medical device.

Alternatively or additionally to any of the examples above, in another example, when coupled, a distal opening of the medical device may be configured to be adjacent to the proximal end of the insert.

In another example, a hub assembly for connection to a medical device may comprise an outer component having a proximal end configured to be connected to a medical device, a distal end, and a cavity extending from the proximal end to the distal end, an inner component having a proximal end, a distal end, and a lumen extending from the proximal end to the distal end positioned at least in part within the cavity of the outer component, and a lumen extending from the proximal end to the distal end of the inner component, the lumen having a taper from a proximal opening to an intermediate region thereof. The distal end of the insert may extend distally beyond the distal end of the outer component and forms a tapered strain relief portion. The outer component may be formed from a first material and the insert is formed from a second material more elastic than the first material.

Alternatively or additionally to any of the examples above, in another example, the inner component may be configured to reduce a volume of the cavity of the outer component and minimize converging of particles from an injected solution.

Alternatively or additionally to any of the examples above, in another example, the outer component may comprise a polycarbonate.

Alternatively or additionally to any of the examples above, in another example, the inner component may comprise a thermoplastic urethane.

In another example, a hub assembly for connection to a medical device may comprise a hub body having a proximal end, a distal end, and a lumen extending therebetween, a deformable region positioned at a location intermediate to the proximal end and the distal end, a docking region positioned adjacent to the deformable region, the docking region having a first stop mechanism positioned on proximal side thereof and a second stop mechanism positioned on a distal side thereof, and ring slidably disposed over the hub body, the ring slidable between the deformable region and the docking region.

Alternatively or additionally to any of the examples above, in another example, when the ring is disposed over the docking region, the deformable region may be in an undeformed state.

Alternatively or additionally to any of the examples above, in another example, when the ring is disposed over the deformable region, the ring may exert a biasing force on the deformable region to bias the deformable region into an elastically deformed state.

Alternatively or additionally to any of the examples above, in another example, when in the elastically deformed state, the deformable region may be biased towards and into the lumen.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
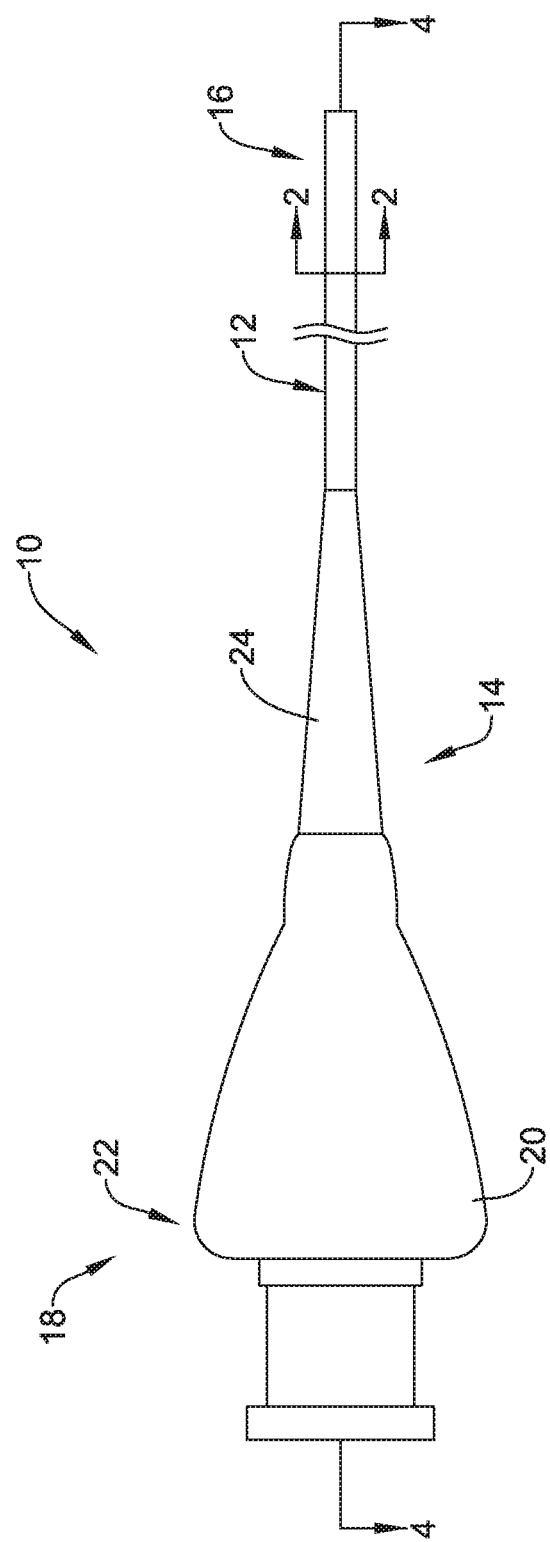
FIG. 1 is a plan view of an illustrative catheter and hub assembly.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

FIG. 1 is a plan view of a catheter 10 in accordance with an embodiment of the present invention. The catheter 10 can be one of a variety of different catheters. In some cases, the catheter 10 may be an intravascular catheter. Examples of some intravascular catheters include microcatheters, drug delivery catheters, diagnostic catheters and guide catheters. FIG. 1 illustrates a microcatheter, but the invention is not limited to such. The intravascular catheter 10 can be manufactured using conventional techniques.

The catheter 10 can be sized in accordance with its intended use. For example, the catheter 10 can have a length that is in the range of about 50 to 200 centimeters and can have a diameter that is in the range of about 1.7 French (F), but can be as large as about 12 F for certain applications.

In the illustrated embodiment, the catheter 10 may include an elongate shaft 12 that has a proximal end 14 and a distal end 16. A hub assembly 18 can be connected to or disposed about the proximal end 14 of the elongate shaft 12. The hub assembly 18 may include a main body portion 20 and a gripping portion 22. In some cases, the hub assembly 18 may include a strain relief 24, although this is not required. When so provided, the strain relief 24 may reduce kinking.

Figure 2:
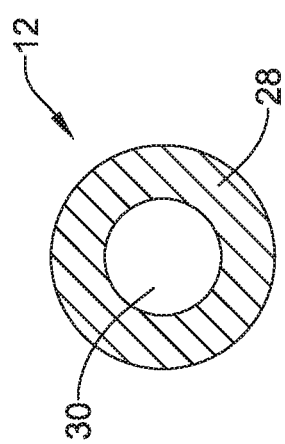
FIG. 2 is a cross-sectional view of the illustrative catheter of FIG. 1, taken at line 2-2.

FIG. 2 is a cross-sectional view of the elongate shaft 12, taken along line 2-2 of FIG. 1. A lumen 30 may extend through the elongate shaft 12 from the proximal end 14 to the distal end 16 thereof. In some embodiments, the elongate shaft 12 may be formed of a single polymer layer 28, which can be any suitable polymeric material, such as, but not limited to, a thermoplastic polymer material. The single polymer layer 28 can be extruded or otherwise formed from a single polymer or from a blend of polymers. The elongate shaft 12 can also include additional polymer layers.

Figure 3:
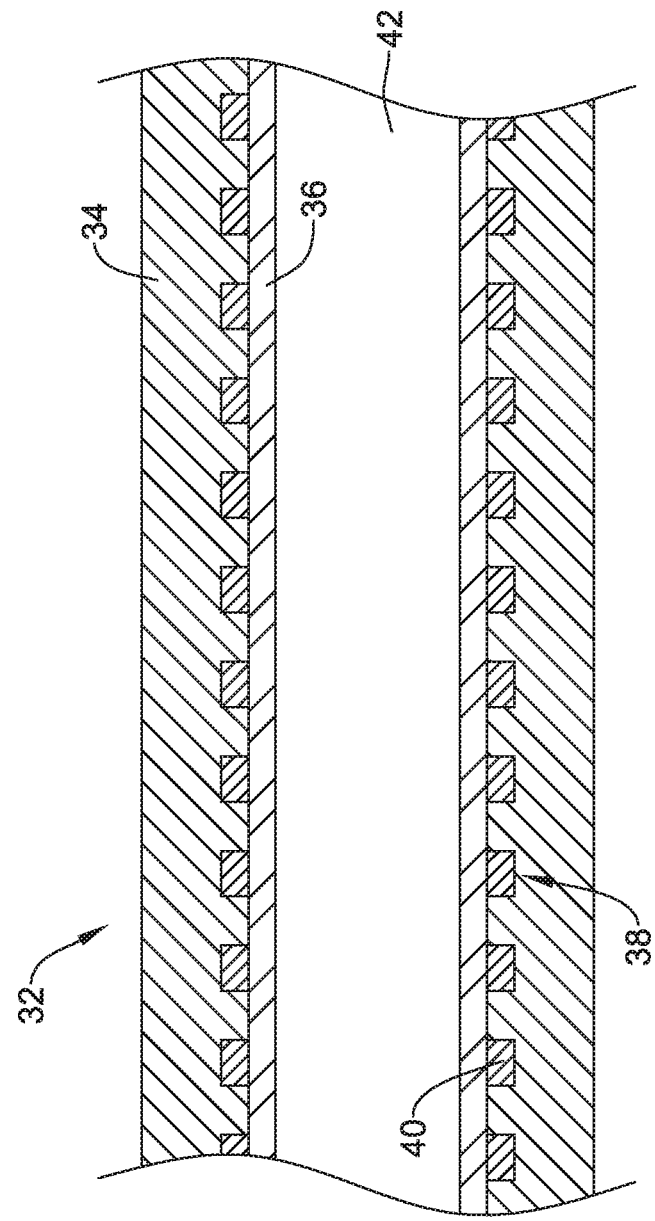
FIG. 3 is an illustrative cross-section of another illustrative catheter.

For example, FIG. 3 illustrates a cross-section of a portion of another exemplary elongate shaft 32 that may be used in place of or in combination with a single layer shaft (e.g., such as the shaft 12). The elongate shaft 32 may include an outer polymer layer 34, an inner polymer layer 36, and an intermediate reinforcing layer 38. In some embodiments, the inner polymer layer 36 can be formed of or include a coating of a material having a suitably low coefficient of friction. Examples of suitable materials include polytetrafluoroethylene (PTFE), better known as TEFLON®. The inner layer 36 can be dimensioned to define a lumen 42 having an appropriate inner diameter to accommodate its intended use. In some embodiments, the inner layer 36 can define a lumen 42 having a diameter of in the range of 0.0160 inches (0.406 millimeters (mm)) to about 0.0170 inches (0.432 mm) or about 0.0165 inches (0.419 mm) and can have a wall thickness in the range of 0.0005 inches (0.0127 mm) to about 0.0015 inches (0.0381 mm), or about 0.001 inches (0.0254 mm). The lumen 42 may extend from a proximal end to a distal end of the elongate shaft 32.

The outer polymer layer 34 can be formed from any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of some suitable materials include polyurethane, elastomeric polyamides, block polyamide/ethers (such as PEBAX), silicones, and co-polymers. The outer layer 34 can be a single polymer, multiple longitudinal sections or layers, or a blend of polymers. By employing careful selection of materials and processing techniques, thermoplastic, solvent soluble, and thermosetting variants of these materials can be employed to achieve the desired results.

In some embodiments, a thermoplastic polymer such as a co-polyester thermoplastic elastomer, for example that available commercially under the ARNITE® name, can be used. The outer layer 34 can have an inner diameter that is about equal to the outer diameter of the inner layer 36. The outer layer 34 can have an inner diameter that is slightly greater than the outer diameter of the inner layer 36 to accommodate the thickness of the reinforcing layer 38.

In some embodiments, the outer layer 34 of the shaft can have an inner diameter in the range of about 0.0165 inches (0.4191 mm) to about 0.153 inches (3.886 mm) and an outer diameter in the range of about 0.023 inches (0.584 mm) to about 0.159 inches (4.039 mm). Part or all of the outer layer 34 can include materials added to increase the radiopacity of the outer layer 34, such as 50% bismuth subcarbonate.

In some embodiments, the reinforcing layer 38 can be positioned between the inner layer 36 and the outer layer 34. A reinforcing braid layer 38 can be formed using a variety of different weave patterns, such as a three-over-three, a four-over-four, and the like. In some embodiments, in order to minimize impact on catheter diameter, the reinforcing layer 38 can be formed from braid wires or a single ribbon 40 or multiple ribbons that are helically wrapped around the inner layer 36.

The braid wires or ribbon 40 can have a rectangular, round, oval or other cross-sectional shape. In some embodiments, the braid wires or ribbon 40 can have a flat cross section such that it has a width that is at least about twice its height. The braid wires or ribbon 40 can be formed of any suitable material, such as stainless steel, tungsten, gold, titanium, silver, copper, platinum or iridium. The braid wires or ribbon 40 can also be formed from non-metallic material such as KEVLAR®. (poly paraphenylene terephthalamide) fibers, LCP (liquid crystal polymer) fibers, or glass fibers and combinations thereof.

Figure 4:
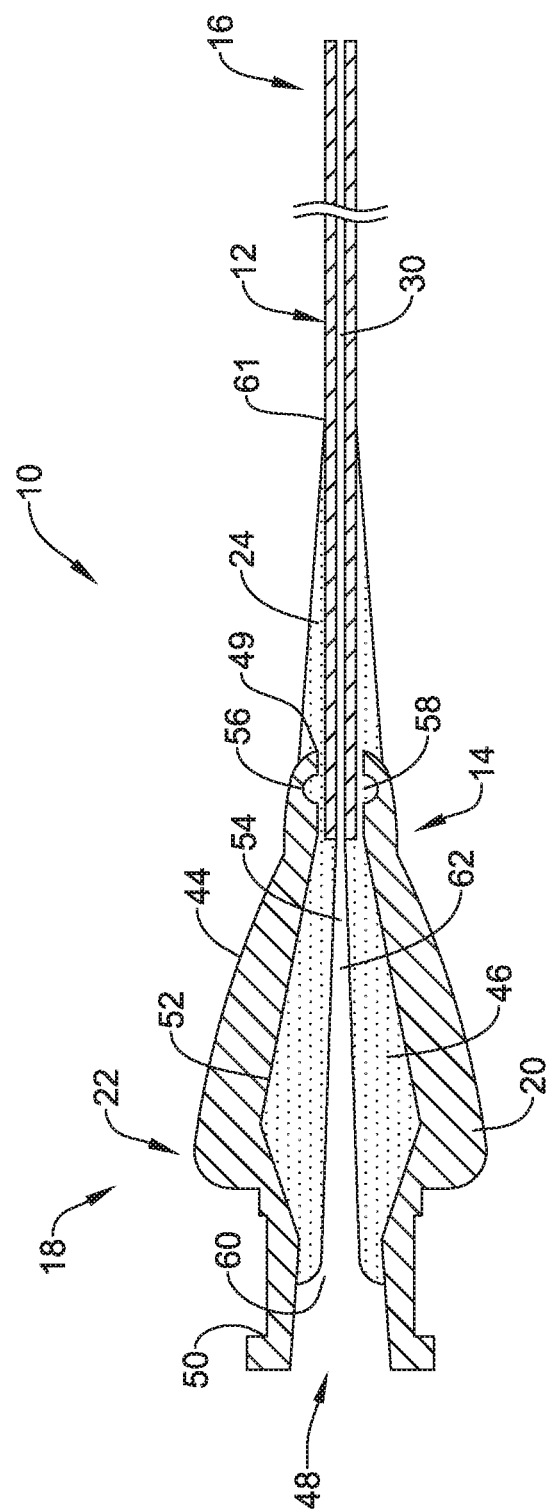
FIG. 4 is a cross-sectional view of the illustrative catheter of FIG. 1, taken at line 4-4.

FIG. 4 is a cross-sectional view of the catheter 10, taken along line 4-4 of FIG. 1. The hub assembly 18 may be connected to the proximal end 14 of the elongate shaft 12, and include an opening 48 and/or other structure to facilitate connection to other medical devices (e.g., syringe, Y-adapter, etc.) and to provide access to the lumen 30 within the shaft 12. The hub assembly 18 may be secured to the catheter shaft 12 at the proximal end 14 of the shaft 12 using any suitable technique, for example, by adhesive, friction fitting, mechanically fitting, chemically bonding, thermally bonding, heat shrink materials, molding, casting, welding (e.g., resistance or laser welding), soldering, brazing, the use of an outer sleeve or polymer layer to bond or connect the components, or the like, or combinations thereof. In some embodiments, the distal end of the hub assembly 18 can be cast, molded or shaped onto the proximal end 14 of the shaft 12 such that it is connected to the proximal end 14.

In some cases, the hub body 20 may include a rigid outer member 44 and a more flexible inner member or insert 46. The outer member 44 may define a large cavity 52 extending from a proximal opening 48 to a distal end 49. The insert 46 may be positioned within the cavity 52. The outer member 44 may be made of a polymeric material such as, but not limited to, a polycarbonate material, or the like, that could be molded or cast. The outer member 44 may include a Luer fitting 50 at a proximal end thereof, or other structure to facilitate connection to another medical device. The outer member 44 may be of conventional design.

In some cases, physicians may use the hub and strain assembly 18 to include a treatment solution. The solution may include particles suspended in a liquid. In some instances, the particles may settle out of the suspension during injection of the solution into the lumen 30 of the elongate shaft 12. This may cause the particles to agglomerate and block the opening to the elongate shaft 12 from the hub assembly 18. In some cases, the volume of the cavity within the hub assembly 18 may contribute to the severity of the agglomeration and/or blockage. For example, the larger the amount of dead space (e.g., the volume in hub cavity), the more particles that can potentially fall out of suspension and dam up, thereby magnifying the blockage of the catheter lumen 30. Dead space may also have a negative impact regarding injection volumes. For example, physicians may have to account for the volume of space in the hub and in the shaft when calculating how much a syringe is capable of injecting. What doesn't get injected is waste. It is further contemplated that hub cavity dimensions and steep transition angles leading into the catheter lumen 30 may also contribute to particle agglomeration. A larger opening at the entrance of the Luer may require more particles from that space to converge at the opening of the shaft lumen 30. This can be a challenge as particles begin to fall out of suspension, creating a higher density as the solution converges.

The insert 46 may help reduce the volume of the cavity 52 of the outer component 44. The insert 46 may be formed from a compliant polymer or other material having elastomeric properties. The insert 46 may be formed from a different material than the outer component 44. Illustrative materials may include, but are not limited to thermoplastic urethanes or silicone. In some cases, the insert 46 may be compliant enough such that it can be formed as separate component from the outer component 44 and inserted into the cavity 52. In such instances, the insert 46 may be deformed (e.g., compressed) to be inserted into the cavity 52 and regain its original shape after insertion. In some embodiments, the insert 46 may be insert molded and/or overmolded within the outer component 44. In some cases, the outer member 44 may include a recess and/or groove 56 configured to receiving a mating protrusion 58 on the insert 46 to form a mechanical interlock between the outer component 44 and the insert 46. The mechanical interlock may help to secure the insert 46 within the outer component 44 and/or reduce or eliminate longitudinal movement of the insert 46 relative to the outer component 44.

In some cases, the strain relief 24 may be formed as a unitary structure with the insert 46. In other words, the strain relief 24 may be built into the insert 46. In other cases, the strain relief 24 may be a separate component from the insert 46. In such instances, the mechanical interlock 56/58 may be used to couple the strain relief 24 to the outer component 44. It is further contemplated that the strain relief 24 and/or the sloped walls of the cavity 52 of the outer component 44 may be sufficient to retain the insert 46 within the cavity 52.

It is contemplated that the insert 46 may be used with existing hub designs which may allow for existing technical features, such as, but not limited to, an ergonomic outer geometry, to remain intact while reducing the overall volume of the hub cavity. In other cases, the insert 46 may be used with new hub designs.

The insert 46 may include a lumen 54 extending between a proximal end or opening 60 of the insert 44 and a distal end of the insert 61. In some cases, the distal end of the insert 61 may be the distal end of the strain relief, as shown in FIG. 4. In other cases, the distal end of the insert 44 may be adjacent to the proximal end 14 of the elongate shaft 12 (e.g., within the outer component 46). The proximal opening 60 of the insert 44 may be positioned distal to the proximal opening 48 of the outer component 46. The lumen 54 may taper (e.g., reduce in diameter) from a proximal opening 60 to an intermediate region 62 thereof, although this is not required. In some embodiments, the lumen 54 may have a constant diameter from the proximal opening 60 to the intermediate region 62. It is further contemplated that the lumen 54 may include changes in diameter other than those shown in FIG. 4. In some cases, the proximal opening 60 may be similar in size to a syringe distal tip. This is just an example. The proximal opening 60 may have any size desired. The insert 46 may reduce the dead space (e.g., volume of a hub cavity) and minimize converging of particles.

Figure 5:
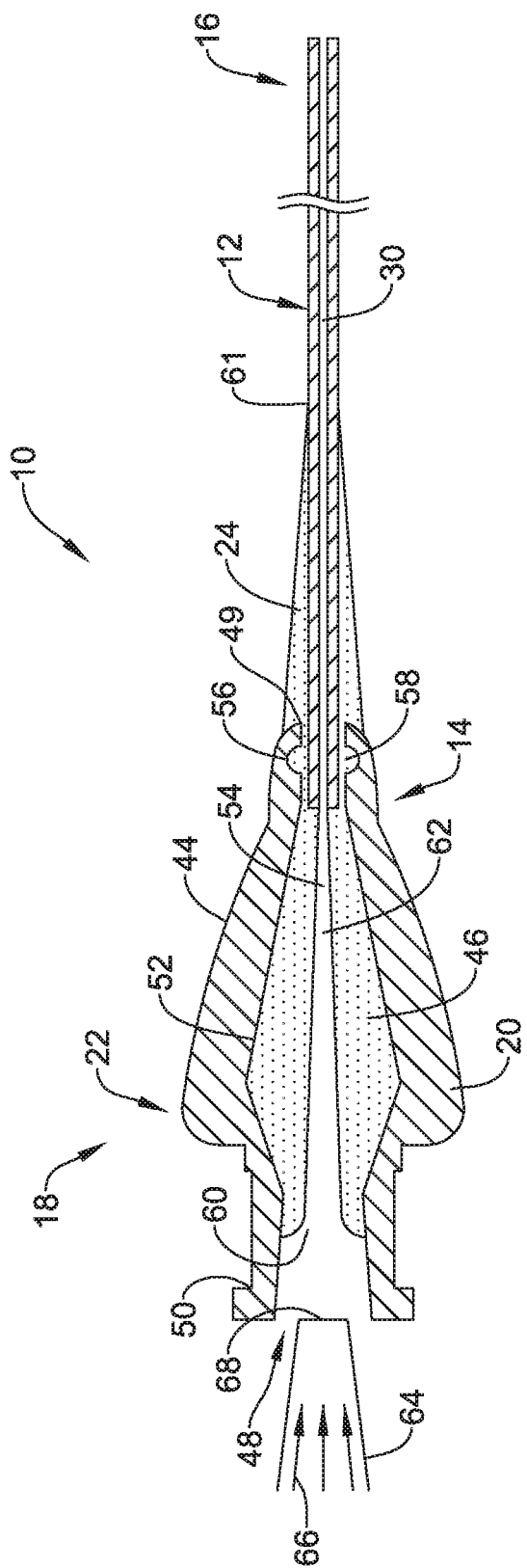
FIG. 5 is a cross-sectional view of the illustrative catheter of FIG. 1, taken at line 4-4 and including a solution delivery device.

FIG. 5 is a cross-sectional view of the catheter 10, as shown in FIG. 4 further including a solution delivery device 64 (such as, but not limited to, a syringe). The solution delivery device 64 may deliver a solution 66 (which may include suspended particles) through the lumen 54 of the insert 46 and to the lumen 30 of the elongate shaft 12. It is contemplated that the distal opening 68 of the delivery device 64 may positioned as close to the proximal opening 60 of the insert 46 as desired. In some cases, the distal opening 68 may be brought into contact with the proximal opening 60 of the insert 46. It is contemplated that the compliant nature of the insert 46 may allow for tactile feedback when the delivery device 64 is engaged with the insert 46 within damaging either the insert 46 or the delivery device 64.

It is contemplated that the insert 46 may provide additional advantages in other medical procedures. For example, when a physician is tasked with implanting embolic coils, they must first position the coil introducer sheath up to the tapered entrance leading into the catheter shaft lumen. In some cases, the sheath may not fit tightly within a hub cavity which may make it a challenge to hold the sheath in line with the catheter shaft. As such, the physician must hold the sheath stationary in the catheter hub with both items (e.g., the hub assembly and the delivery sheath) in one hand, while delivering the coil with the other hand. It may be difficult to keep the sheath positioned tight against the internal hub body and hold the hub. Often this necessitates the help of an assistant. The procedure basically requires three hands in total to deliver the coil properly. It may be desirable to allow for the delivery of an embolic coil without necessitating the use of an assistant.

Figure 6:
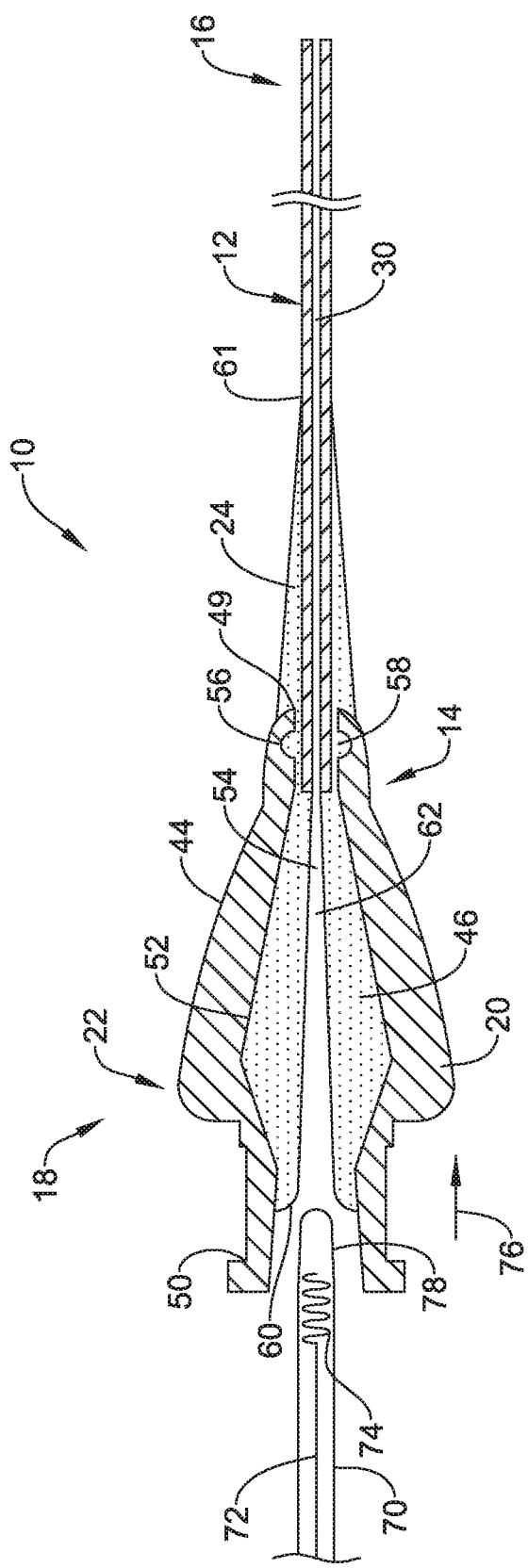
FIG. 6 is a cross-sectional view of the illustrative catheter of FIG. 1, taken at line 4-4 and including a delivery sheath in a first configuration.
Figure 7:
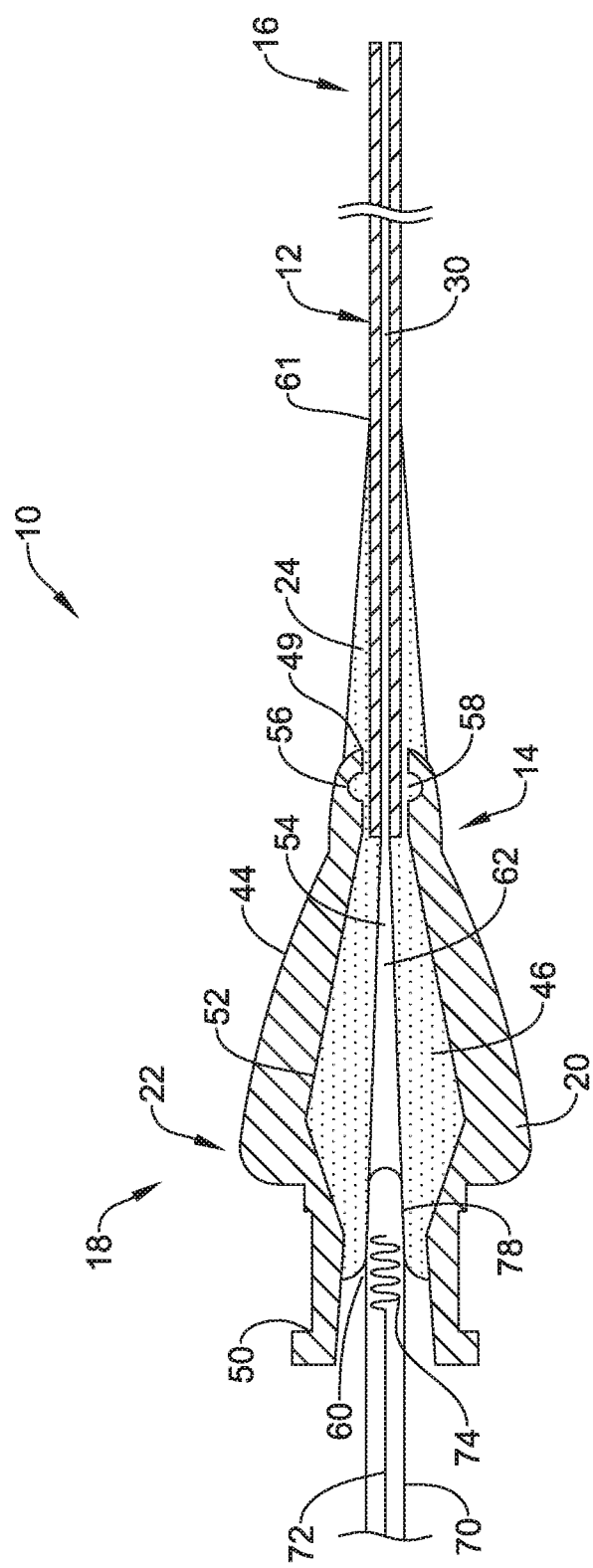
FIG. 7 is another configuration of the system of FIG. 6.

FIG. 6 is a cross-sectional view of the catheter 10, as shown in FIG. 4 further including delivery sheath 70 and embolic coil delivery device 72. The embolic coil delivery device 72 may include an embolic coil 74. It is contemplated that other medical devices may be used in place of or in addition to the delivery sheath 70. While a delivery of an embolic coil is used for an example, the concepts apply to any other medical device that may be used in combination with the catheter 10. In addition to reducing the volume of the cavity within the hub assembly 18, the insert 46 may also retain the coil delivery sheath 70 in place at or near the entrance of the lumen 30 of the catheter shaft 12. For example, the delivery sheath 70 may be distally advanced, as shown at arrow 76, until a distal end region 78 of the delivery sheath 70 forms an interference, or friction, fit with the lumen 54 of the insert 46, as shown in FIG. 7. In some cases, the distal end region 78 of the delivery sheath 70 may be positioned closer to the opening of the lumen 30 than what is shown in FIG. 7. The interference fit may allow the insert 46 to "hug" or hold the delivery sheath 70 as it is pushed into place, where it will remain seated without the need for a physician (or assistant) to hold it in place.

In some instances, the lumen 54 of the insert 46 may be provided with texturing configured to further grip the delivery sheath 70. For example, the surface of, or a portion of the surface of, the lumen 54 of the insert 46 may be provided with bumps, grooves, ridges, or other texturizing characteristics configured to increase the surface area and/or improved the friction fit between the surface of the lumen 54 and the delivery sheath 70. It is further contemplated that the lumen 54 of the insert 46 may include a stop mechanism configured to limit distal advancement of the sheath 70. In some cases, the stop mechanism may include a mechanical stop that physically stops distal advancement, such as, but not limited to a reduction in diameter of the lumen 54. In other cases, the stop mechanism may be a change of material which provides a tactile indication to the physician that the target location has been reached.

Such a seated arrangement may reduce the risk of the coil 74 being damaged during delivery into the catheter shaft 12. For example, it may minimize the chance of damage to the tip of the coil 74 and/or loosening of the attachment of the coil 74 to the delivery device 72 within the hub cavity. Further, the seated arrangement may make the procedure less awkward and cumbersome process for the physician.

Figure 8:
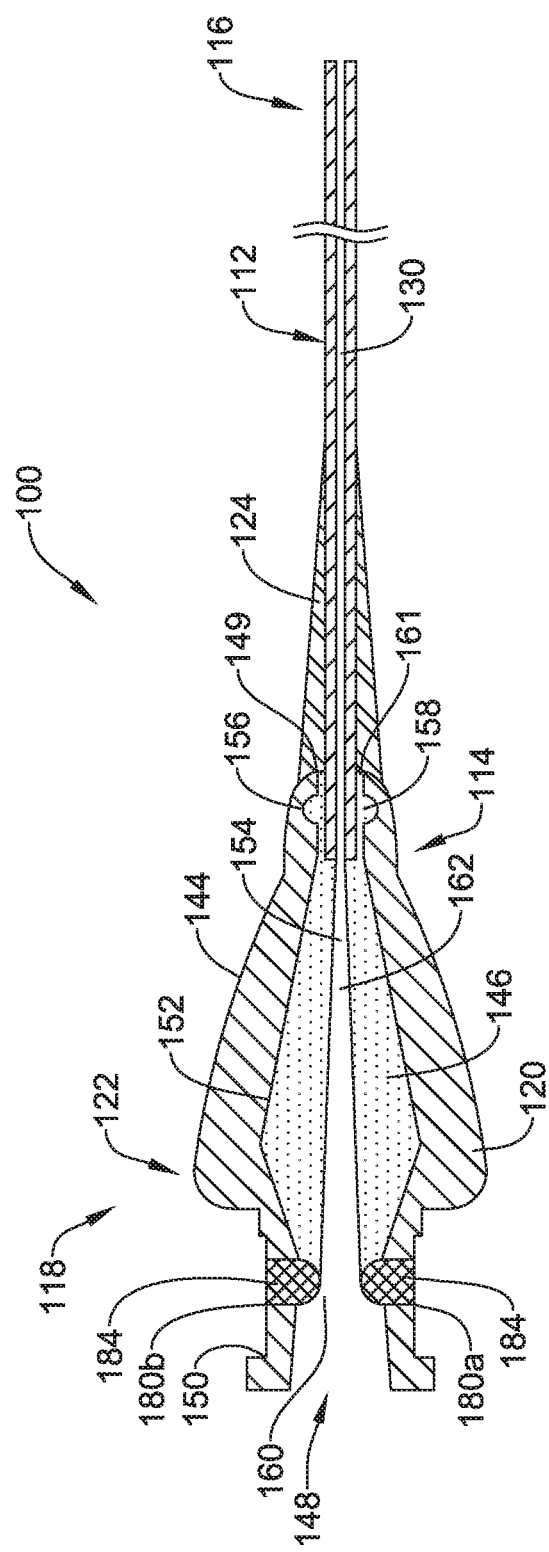
FIG. 8 is a cross-sectional view of another illustrative catheter in a first configuration.

FIG. 8 is a cross-sectional view of another illustrative catheter 100. The catheter 100 may be similar in form and function to the catheter 10 described above. In the illustrated embodiment, the catheter 100 may include an elongate shaft 112 that has a proximal end 114 and a distal end 116. A hub assembly 118 can be connected to or disposed about the proximal end 114 of the elongate shaft 112. The hub assembly 118 may include a main body portion 120 and a gripping portion 122. In some cases, the hub assembly 118 may include a strain relief 124, although this is not required. When so provided, the strain relief 124 may reduce kinking.

The hub assembly 118 may be connected to the proximal end 114 of the elongate shaft 112, and include an opening 148 and/or other structure to facilitate connection to other medical devices (e.g., syringe, Y-adapter, etc.) and to provide access to lumen 130 within the shaft 112. The hub assembly 118 may be secured to the catheter shaft 112 at the proximal end 114 of the shaft 112 using any suitable technique, for example, by adhesive, friction fitting, mechanically fitting, chemically bonding, thermally bonding, heat shrink materials, molding, casting, welding (e.g., resistance or laser welding), soldering, brazing, the use of an outer sleeve or polymer layer to bond or connect the components, or the like, or combinations thereof. In some embodiments, the distal end of the hub assembly 118 can be cast, molded or shaped onto the proximal end 114 of the shaft 112 such that it is connected to the proximal end 114.

In some cases, the hub body 120 may include a rigid outer member 144 and a more flexible inner member or insert 146. The insert 146 may be similar in form and function to the insert 46 described above. The outer member 144 may define a large cavity 152 extending from a proximal opening 148 to a distal end 149. The insert 146 may be positioned within the cavity 152. The outer member 144 may be made of a polymeric material such as, but not limited to, a polycarbonate material, or the like, that could be molded or cast. The outer member 144 may include a Luer fitting 150, or other structure to facilitate connection to another medical device.

The insert 146 may help reduce the volume of the cavity 152 of the outer component 144. The insert 146 may be formed from a compliant polymer or other material having elastomeric properties. Illustrative materials may include, but are not limited to thermoplastic urethanes or silicone. In some cases, the insert 146 may be compliant enough such that it can be formed as separate component from the outer component 144 and inserted into the cavity 152. In such instances, the insert 146 may be deformed (e.g., compressed) to be inserted into the cavity 152 and regain its original shape after insertion. In some embodiments, the insert 146 may be insert molded and/or overmolded within the outer component 144. In some cases, the outer member 144 may include a recess and/or groove 156 configured to receiving a mating protrusion 158 on the insert 146 to form a mechanical interlock between the outer component 144 and the insert 146. The mechanical interlock may help to secure the insert 146 within the outer component 144 and/or reduce or eliminate longitudinal movement of the insert 146 relative to the outer component 144.

In some cases, the strain relief 124 may be formed as a unitary structure with the insert 146. In other words, the strain relief 124 may be built into the insert 146. In other cases, the strain relief 124 may be a separate component from the insert 146. In such instances, the mechanical interlock 156/158 may be used to couple the strain relief 124 to the outer component 144. It is further contemplated that the strain relief 124 and/or the sloped walls of the cavity 152 of the outer component 144 may be sufficient to retain the insert 146 within the cavity 152.

The insert 146 may include a lumen 154 extending between a proximal end or opening 160 of the insert 146 and a distal end of the insert 161. In some cases, the distal end of the insert 146 may be the distal end of the strain relief 124. In other cases, the distal end 161 of the insert 146 may be adjacent to the proximal end 114 of the elongate shaft 112 (e.g., within the outer component 144). The lumen 154 may taper (e.g., reduce in diameter) from a proximal opening 160 to an intermediate region 162 thereof, although this is not required. In some embodiments, the lumen 154 may have a constant diameter from the proximal opening 160 to the intermediate region 162. It is further contemplated that the lumen 154 may include changes in diameter other than those shown in FIG. 8. In some cases, the proximal opening 160 may be similar in size to a syringe distal tip. This is just an example. The proximal opening 160 may have any size desired. The insert 146 may reduce the dead space (e.g., volume of a hub cavity) and minimize converging of particles.

In some embodiments, the outer member 144 may include one or more windows, openings, or through holes 180a, 180b (collectively 180) extending through the wall thereof and from an inner surface to an outer surface of the outer member 144. The openings 180 may be filled with a compliant polymer or other material having elastomeric properties to form one or more depressible regions 184 (e.g., regions that are elastically deformable or movable). In some cases, the depressible regions 184 may be formed as a unitary structure with the insert 146. In other cases, the depressible regions 184 may be a separate component from the insert 146. It is further contemplated that the insert 146 and the depressible regions 184 may be formed from the same or different materials, as desired.

The hub assembly 118 may include, one, two, three, four, or more depressible regions 184. The depressible regions 184 may be asymmetrically or symmetrically distributed about an outer perimeter of the hub assembly 118. In one example, two depressible regions 184 may be positioned approximately 180° (about the perimeter) from one another such that there is a depressible region 184 positioned on opposing sides of a longitudinal axis of the hub assembly. Alternatively, the depressible region 184 may be a single opening 180 which may extend completely around the perimeter (e.g., 360°) or any portion of the perimeter less than 360°. It is further contemplated that while the depressible regions 184 are positioned adjacent to the proximal opening 148, the depressible regions 184 may be positioned anywhere along a length of the hub assembly 118.

Figure 9:
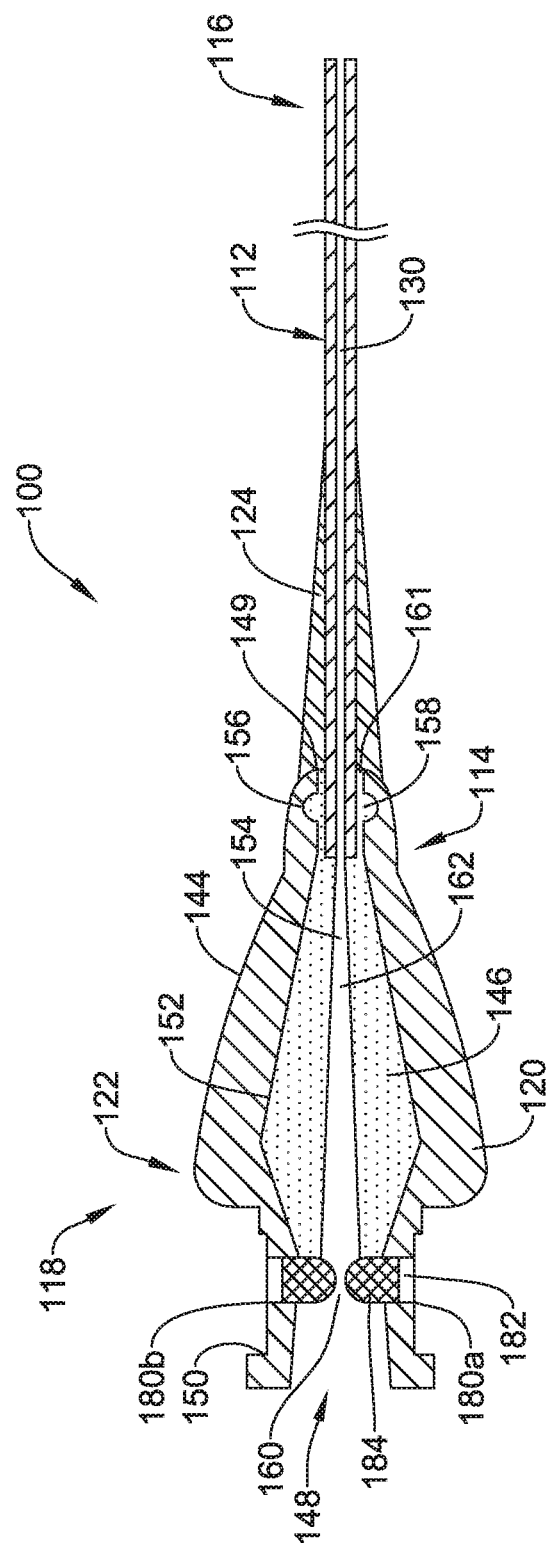
FIG. 9 is the illustrative catheter of FIG. 8 in a second configuration.
Figure 10:
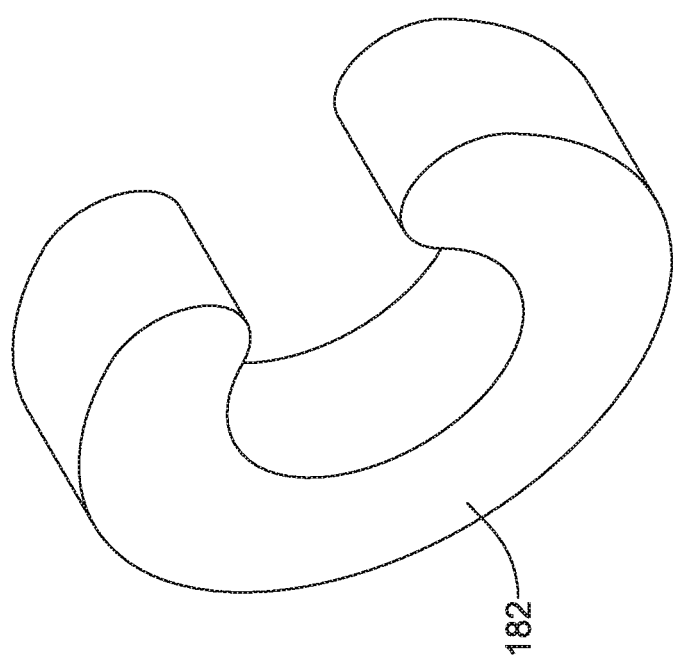
FIG. 10 is a perspective view of an illustrative clamping mechanism.

The depressible regions 184 may be deformable under an applied pressure. For example, a clamping mechanism 182 may be removably positioned over the depressible regions 184 to bias the depressible regions 184 inwards (e.g., away from an exterior surface and towards a center of the outer component 146) as shown in FIG. 9. In some cases, the clamping mechanism 182 may be a clip having a generally "C" shape, as shown in FIG. 10. Other shaped clips, such as, but not limited to "U"-shaped are also contemplated. In some cases, the clamping mechanism 182 may be used in combination with the depressible regions 184 to temporarily exert a clamping force on a device (such as the delivery sheath 70 described above) within the opening 148 and/or the lumen 154 to maintain the device in a desired position.

Figure 11:
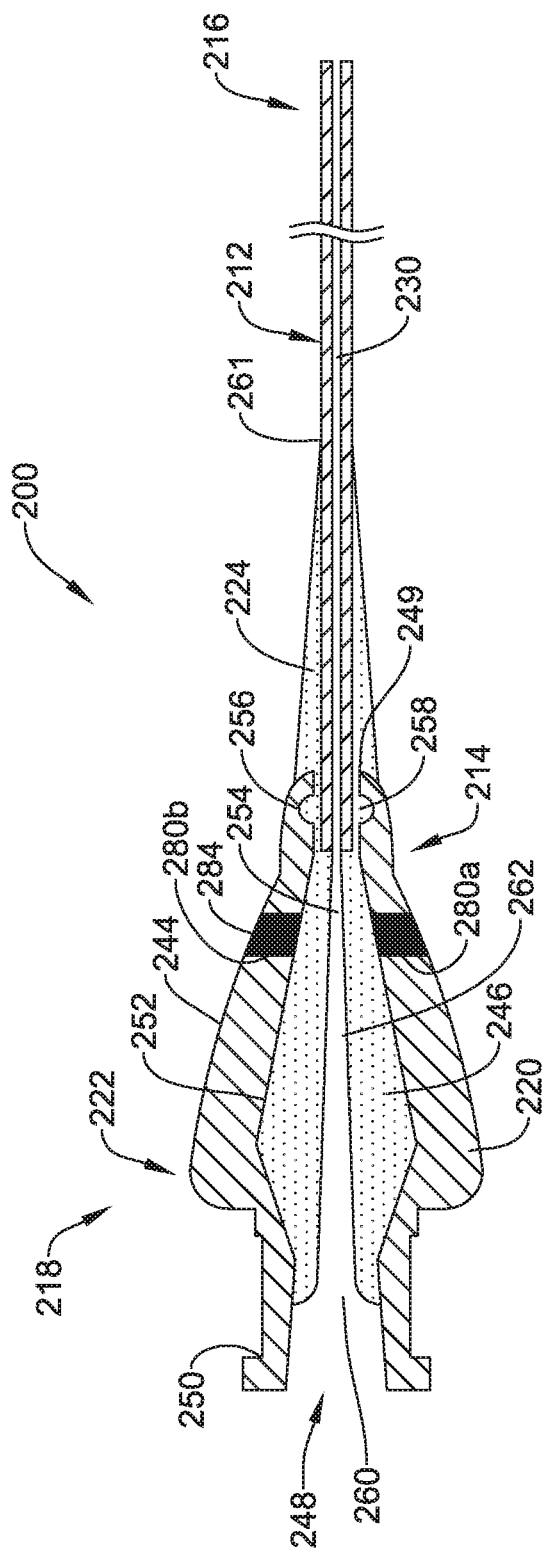
FIG. 11 is a cross-sectional view of another illustrative catheter.

FIG. 11 is a cross-sectional view of another illustrative catheter 200. The catheter 200 may be similar in form and function to the catheters 10, 100 described above. In the illustrated embodiment, the catheter 200 may include an elongate shaft 212 that has a proximal end 214 and a distal end 216. A hub assembly 218 can be connected to or disposed about the proximal end 214 of the elongate shaft 212. The hub assembly 218 may include a main body portion 220 and a gripping portion 222. In some cases, the hub assembly 218 may include a strain relief 224, although this is not required. When so provided, the strain relief 224 may reduce kinking.

The hub assembly 218 may be connected to the proximal end 214 of the elongate shaft 212, and include an opening 248 and/or other structure to facilitate connection to other medical devices (e.g., syringe, Y-adapter, etc.) and to provide access to lumen 230 within the shaft 212. The hub assembly 218 may be secured to the catheter shaft 212 at the proximal end 214 of the shaft 212 using any suitable technique, for example, by adhesive, friction fitting, mechanically fitting, chemically bonding, thermally bonding, heat shrink materials, molding, casting, welding (e.g., resistance or laser welding), soldering, brazing, the use of an outer sleeve or polymer layer to bond or connect the components, or the like, or combinations thereof. In some embodiments, the distal end of the hub assembly 218 can be cast, molded or shaped onto the proximal end 214 of the shaft 212 such that it is connected to the proximal end 214.

In some cases, the hub body 220 may include a rigid outer member 244 and a more flexible inner member or insert 246. The insert 246 may be similar in form and function to the insert 46 described above. The outer member 244 may define a large cavity 252 extending from a proximal opening 248 to a distal end 249. The insert 246 may be positioned within the cavity 252. The outer member 244 may be made of a polymeric material such as, but not limited to, a polycarbonate material, or the like, that could be molded or cast. The outer member 244 may include a Luer fitting 250, or other structure to facilitate connection to another medical device.

The insert 246 may help reduce the volume of the cavity 252 of the outer component 244. The insert 246 may be formed from a compliant polymer or other material having elastomeric properties. Illustrative materials may include, but are not limited to thermoplastic urethanes or silicone. In some cases, the insert 246 may be compliant enough such that it can be formed as separate component from the outer component 244 and inserted into the cavity 252. In such instances, the insert 246 may be deformed (e.g., compressed) to be inserted into the cavity 252 and regain its original shape after insertion. In some embodiments, the insert 246 may be insert molded and/or overmolded within the outer component 244. In some cases, the outer member 244 may include a recess and/or groove 256 configured to receiving a mating protrusion 258 on the insert 246 to form a mechanical interlock between the outer component 244 and the insert 246. The mechanical interlock may help to secure the insert 246 within the outer component 244 and/or reduce or eliminate longitudinal movement of the insert 246 relative to the outer component 244.

In some cases, the strain relief 224 may be formed as a unitary structure with the insert 246. In other words, the strain relief 224 may be built into the insert 246. In other cases, the strain relief 224 may be a separate component from the insert 246. In such instances, the mechanical interlock 256/258 may be used to couple the strain relief 224 to the outer component 244. It is further contemplated that the strain relief 224 and/or the sloped walls of the cavity 252 of the outer component 244 may be sufficient to retain the insert 246 within the cavity 252.

The insert 246 may include a lumen 254 extending between a proximal end or opening 260 of the insert 246 and a distal end of the insert 261. In some cases, the distal end of the insert 261 may be the distal end of the strain relief, as shown in FIG. 11. In other cases, the distal end of the insert 246 may be adjacent to the proximal end 214 of the elongate shaft 212 (e.g., within the outer component 244). The lumen 254 may taper (e.g., reduce in diameter) from a proximal opening 260 to an intermediate region 262 thereof, although this is not required. In some embodiments, the lumen 254 may have a constant diameter from the proximal opening 260 to the intermediate region 262. It is further contemplated that the lumen 254 may include changes in diameter other than those shown in FIG. 11. In some cases, the proximal opening 260 may be similar in size to a syringe distal tip. This is just an example. The proximal opening 260 may have any size desired. The insert 246 may reduce the dead space (e.g., volume of a hub cavity) and minimize converging of particles.

In some embodiments, the outer member 244 may include one or more windows or openings 280a, 280b (collectively 280) extending from an inner surface to an outer surface of the outer member 244. The openings 280 may be filled with a compliant polymer or other material having elastomeric properties to form one or more depressible regions 284. In some cases, the depressible regions 284 may be formed as a unitary structure with the insert 246. In other cases, the depressible regions 284 may be a separate component from the insert 246. It is further contemplated that the insert 244 and the depressible regions 284 may be formed from the same or different materials, as desired.

The hub assembly 218 may include, one, two, three, four, or more depressible regions 284. The depressible regions 284 may be asymmetrically or symmetrically distributed about an outer perimeter of the hub assembly 218. In one example, two depressible regions 284 may be positioned approximately 280° (about the perimeter) from one another such that there is a depressible region 284 positioned on opposing sides of a longitudinal axis of the hub assembly. Alternatively, the depressible region 284 may be a single opening 280 which may extend completely around the perimeter (e.g., 360°) or any portion of the perimeter less than 360°. It is further contemplated that while the depressible regions 284 are positioned adjacent to the proximal opening 248, the depressible regions 284 may be positioned anywhere along a length of the hub assembly 218.

The depressible regions 284 may be deformable under an applied pressure. For example, a clamping mechanism, such as, but not limited to the c-clip 182 shown in FIG. 10, may be removably positioned over the depressible regions 284 to bias the depressible regions 284 inwards (e.g., away from an exterior surface). In some cases, the clamping mechanism may be a clip having a generally "C" shape, as shown in FIG. 10. Other shaped clips, such as, but not limited to "U"-shaped are also contemplated. In some cases, the clamping mechanism may be used in combination with the depressible regions 284 to temporarily exert a clamping force on a device (such as the delivery sheath 70 described above) within the opening 248 and/or the lumen 254 to maintain the device in a desired position.

Figure 12A:
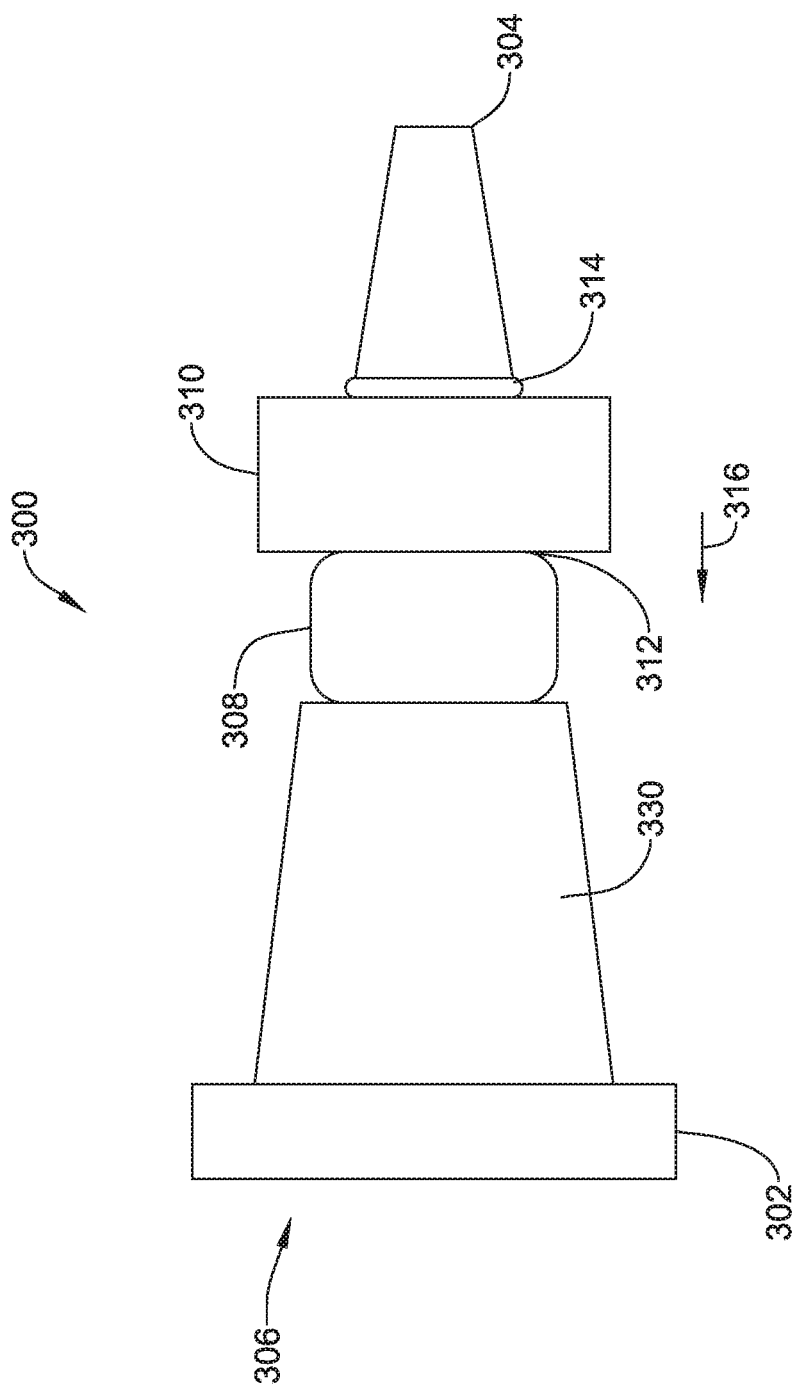
FIG. 12A is a side view of an illustrative hub for use with a medical device in a first configuration.
Figure 12B:
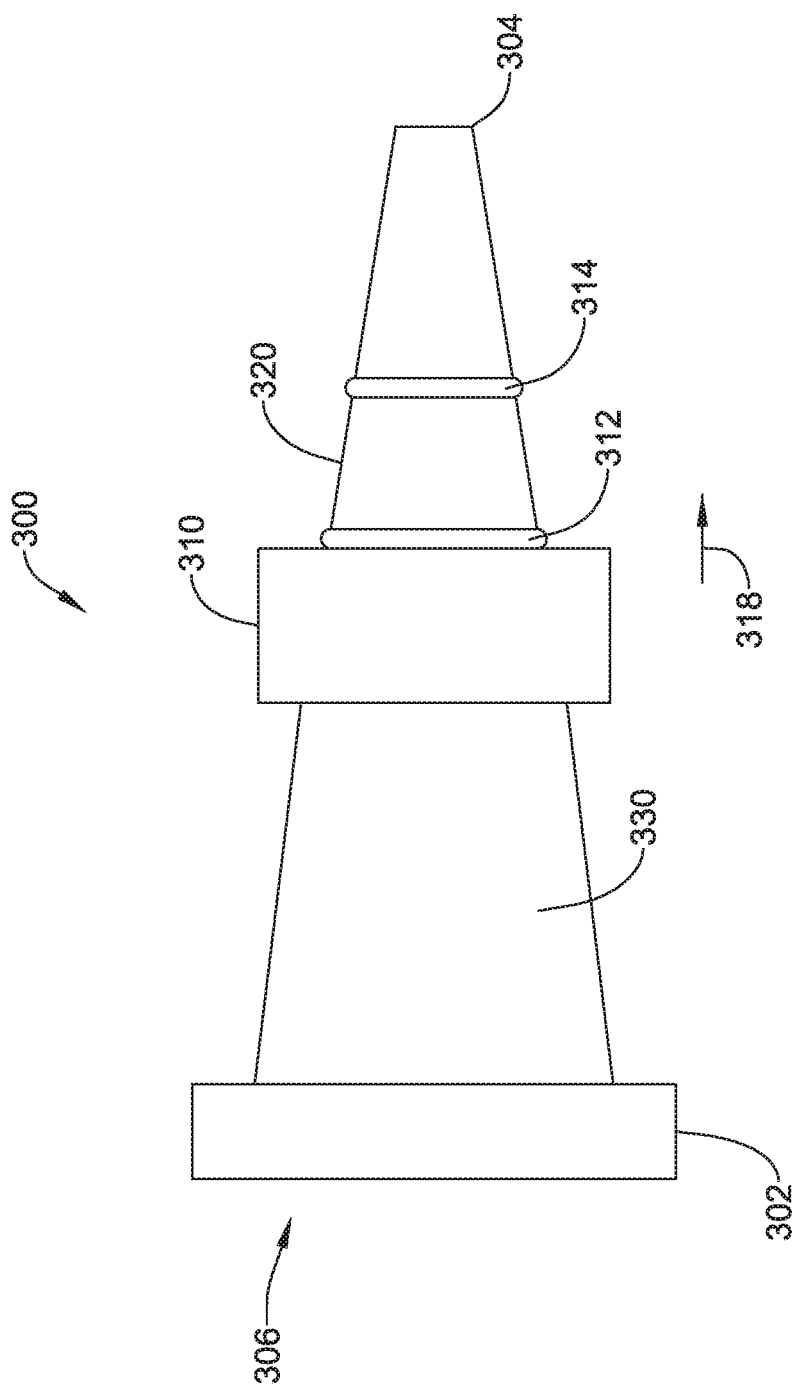
FIG. 12B is the illustrative hub of FIG. 12A in a second configuration.

FIGS. 12A and 12B are side views of another illustrative hub assembly 300 that may be used with any of the catheters 10, 100, 200 described above. The hub assembly 300 may include a hub body 330 having a proximal end 302 and a distal end 304. The proximal end 302 may include a Luer fitting, or other structure to facilitate connection to another medical device. A lumen 306 may extend from the proximal end 302 to the distal end 304. The hub assembly 300 may be configured to be connected to the proximal end of an elongate shaft. The lumen 306 of the hub assembly 300 may be in communication with the lumen of the shaft. The hub assembly 300 may be secured to the catheter shaft at the proximal end of the shaft using any suitable technique, for example, by adhesive, friction fitting, mechanically fitting, chemically bonding, thermally bonding, heat shrink materials, molding, casting, welding (e.g., resistance or laser welding), soldering, brazing, the use of an outer sleeve or polymer layer to bond or connect the components, or the like, or combinations thereof. In some embodiments, the distal end 304 of the hub assembly 300 can be cast, molded or shaped onto the proximal end of the shaft such that it is connected to the proximal end thereof.

The hub assembly 300 may include a compliant or deformable region 308 positioned at a location intermediate to the proximal end 302 and the distal end 304. The deformable region 308 may be formed from a compliant polymer or other material having elastomeric properties which is capable of being temporarily deformed in the presence of a biasing force. The remainder of the hub assembly 300 may be formed from a polymeric material that may be more rigid than the deformable region 308 such as, but not limited to, a polycarbonate material, or the like, that could be molded or cast. When the biasing force is removed, the deformable region 308 may automatically return to its original (undeformed) state. The hub assembly 300 may further include a slidable ring 310. It is contemplated that the ring 310 may have any outer shape desired. The inner surface of the ring 310 may be sized and shaped to be approximately the same size and shape of the hub assembly 300 at the landing or docking region 320.

The ring 310 may be configured to be proximally retracted, as shown at arrow 316, from a landing region 320 to the deformable region 308. The deformable region 308 may have any outer diameter that is larger than an inner diameter of the ring 310. This may cause the inner surface of the ring 310 to exert a biasing force on the deformable region 308 (when disposed over the deformable region, as in FIG. 12B). This may move (e.g., deform) the deformable region 308 inwards (e.g., away from an exterior surface) and into the lumen 306. In some cases, the ring 310 may be used in combination with the deformable region 308 to temporarily exert a clamping force on a device (such as the delivery sheath 70 described above) within the lumen 306 to maintain the device in a desired position.

In an illustrative example, a device, such as, but not limited to, a delivery sheath, may be advanced into the lumen 306 of the hub assembly 300. When the device is located in its desired position, the ring 310 may be proximally retracted 316 from the docking region 320 to the deformable region 308 to the configuration shown in FIG. 12B. This may exert a force (e.g., friction force, clamping force, etc.) on the device thus preventing or limiting proximal or distal (and/or rotational) movement of the device. When the procedure is complete, or the device is no longer needed, the ring may be advanced distally, as shown at arrow 318, from the deformable region 308 to the landing region 320, returning the hub assembly 300 to the configuration shown in FIG. 12A. In some embodiments, the hub assembly 300 may include a proximal stop mechanism 312 and a distal stop mechanism 314 located on either side of the landing region 320. The stop mechanisms 312, 314 may maintain the ring 310 within the landing region 320, until moved by a physician, to prevent or limit unintentional movement of the ring 310. The stop mechanisms 312 may be sized and shaped to prevent unintended movement of the ring 310, but also to allow the physician to move the ring 310 with relative ease.

In some instances, the deformable region 308 may also function as a hemostasis seal whether or not a device is disposed within the lumen 306 of the hub assembly 300. For example, when a device is absent from the lumen 306 of the hub assembly 300, the ring 310 may be proximally retracted 316 from the docking region 320 to the deformable region 308 to the configuration shown in FIG. 12B. This may cause the deformable region 308 to deform inwardly such that the inner portion (e.g., an inner circumference or perimeter) of the deformable region 308 comes into contact with itself effectively forming a seal to prevent the flow of blood or other fluids through the lumen 306 of the hub assembly 300.

The materials that can be used for the various components of the medical devices and/or systems 10, 100, 200, 300 (and/or other systems disclosed herein) and the various elements thereof disclosed herein may include those commonly associated with medical devices. For simplicity purposes, the following discussion makes reference to the catheter 10. However, this is not intended to limit the devices and methods described herein, as the discussion may be applied to other elements, members, components, or devices disclosed herein, such as, but not limited to, the elongate shafts 12, 112, 212 and the hub assembly 18, 118, 218, 300 and/or elements or components thereof.

In some embodiments, the catheter 10, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter 10, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10. For example, catheter 10, and/or components or portions thereof, may be made of a material that does not substantially distort the image and create substantial artifacts (e.g., gaps in the image). Certain ferromagnetic materials, for example, may not be suitable because they may create artifacts in an MRI image. The catheter 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, an exterior surface of the medical device system 10 (including, for example, an exterior surface of the delivery system) may be sandblasted, bead-blasted, sodium bicarbonate-blasted, electropolished, etc. In these as well as in some other embodiments, a coating, for example a lubricious, a hydrophilic, a protective, or other type of coating may be applied over portions or all of the outer sheath, or in embodiments without an outer sheath over portions of the delivery system, or other portions of the medical device system 10. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A hub assembly for connection to a medical device, the hub assembly comprising:
   an outer component having a proximal end, a distal end, and a cavity extending from the proximal end to the distal end;
   an insert having a proximal end, a distal end, and a lumen extending from the proximal end of the insert to the distal end of the insert, the insert positioned at least in part within the cavity of the outer component;
   one or more windows extending through a wall of the outer component, the one or more windows filled with a compliant material to form one or more elastically deformable regions in the outer component; and
   a clamping mechanism configured to be removably positioned over the one or more elastically deformable regions;
   wherein the outer component is formed from a first material and the insert is formed from a second material different from the first material; and
   wherein the lumen of the insert tapers from a proximal opening of the lumen of the insert to an intermediate region of the lumen of the insert.

2. The hub assembly of claim 1, wherein the second material is more compliant than the first material.

3. The hub assembly of claim 1, wherein the one or more elastically deformable regions forms a unitary structure with the insert.

4. The hub assembly of claim 1, wherein the one or more elastically deformable regions are separate components from the insert.

5. The hub assembly of claim 1 wherein the clamping mechanism is configured to exert biasing force on an outer surface of the one or more elastically deformable regions to deform the one or more elastically deformable regions towards a center of the outer component.

6. The hub assembly of claim 1, wherein the distal end of the insert extends distally beyond the distal end of the outer component.

7. The hub assembly of claim 6, wherein a portion of the insert extending distally beyond the distal end of the outer component forms a tapered strain relief portion.

8. The hub assembly of claim 1, wherein the distal end of the outer component is configured to be coupled to the medical device.

9. The hub assembly of claim 8, wherein, when coupled, a distal opening of the medical device is configured to be adjacent to the proximal end of the insert.

10. A hub assembly for connection to a medical device, the hub assembly comprising:
    an outer component having a proximal end configured to be connected to the medical device, a distal end, and a cavity extending from the proximal end to the distal end;
    one or more elastically deformable regions formed in a wall of the outer component;
    an inner component positioned at least in part within the cavity of the outer component, the inner component having a proximal end, a distal end, and a lumen extending from the proximal end of the inner component to the distal end of the inner component; and
    a clamping mechanism configured to be removably positioned over the one or more elastically deformable regions;
    wherein the lumen of the inner component tapers from a proximal opening of the lumen of the inner component to an intermediate region of the lumen of the inner component;

wherein the distal end of the inner component extends distally beyond the distal end of the outer component and forms a tapered strain relief portion; and wherein the outer component is formed at least in part from a first material and the inner component is formed from a second material more elastic than the first material.

11. The hub assembly of claim 10, wherein the inner component is configured to reduce a volume of the cavity of the outer component and minimize converging of particles from an injected solution.

12. The hub assembly of claim 10, wherein the outer component comprises a polycarbonate.

13. The hub assembly of claim 10, wherein the inner component comprises a thermoplastic urethane.

* * * * *